United States Patent
Tittmann et al.

[11] Patent Number: 5,871,669
[45] Date of Patent: Feb. 16, 1999

[54] STABILIZER COMBINATION

[75] Inventors: Rolf Tittmann, Lörrach, Germany; Francesco Fuso, Therwil, Switzerland; Gerhard Reinert, Allschwil, Switzerland; Hans Peter Härri, Reinach, Switzerland

[73] Assignee: Ciba Specialty Chemicals Corporation, Tarrytown, N.Y.

[21] Appl. No.: 814,301

[22] Filed: Mar. 10, 1997

[30] Foreign Application Priority Data

Mar. 13, 1996 [CH] Switzerland ............... 663/96

[51] Int. Cl.⁶ .................................................. C09K 15/26
[52] U.S. Cl. ........................................................ 252/402
[58] Field of Search ............................................. 252/402

[56] References Cited

U.S. PATENT DOCUMENTS

| | | | |
|---|---|---|---|
| 3,293,249 | 12/1966 | Biland et al. | 260/248 |
| 3,334,046 | 8/1967 | Dexter et al. | 252/402 |
| 3,397,205 | 8/1968 | Laethi et al. | 260/248 |
| 3,709,883 | 1/1973 | Dexter et al. | 252/402 |
| 3,896,125 | 7/1975 | Helmo et al. | 260/249.5 |
| 4,831,068 | 5/1989 | Reinert et al. | 524/100 |
| 5,649,980 | 7/1997 | Reinehr et al. | 8/566 |
| 5,668,200 | 9/1997 | Valet et al. | 524/100 |

FOREIGN PATENT DOCUMENTS

| | | |
|---|---|---|
| 0584044 | 2/1994 | European Pat. Off. |
| 1241452 | 6/1967 | Germany |
| 1670332 | 3/1972 | Germany |
| 1176770 | 7/1968 | United Kingdom |
| 1183946 | 3/1970 | United Kingdom |

OTHER PUBLICATIONS

Helv. Chim. Acta, vol. 55, No. 1, pp. 1566–1595 (1972).

*Primary Examiner*—Kriellion S. Morgan
*Attorney, Agent, or Firm*—David R. Crichton

[57] ABSTRACT

A description is given of novel stabilizer mixtures comprising at least one compound of the formula

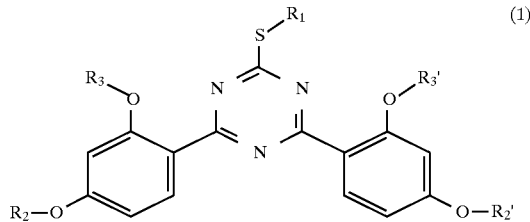

and at least one compound of the formula

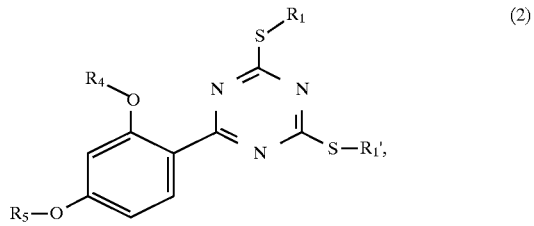

in which the variables are as defined in the claims. The novel stabilizer mixtures are suitable for stabilizing organic material, especially textile fibre materials, against damage by light, oxygen and heat.

11 Claims, No Drawings

STABILIZER COMBINATION

The present invention relates to novel stabilizer mixtures comprising mono- und bis-resorcinyltriazines, processes for their preparation, and their use for the photochemical and chemical stabilization of organic material, preferably undyed or dyed textile fibre materials.

The invention provides stabilizer mixtures comprising at least one compound of the formula

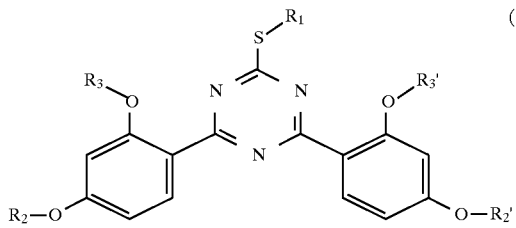

and at least one compound of the formula

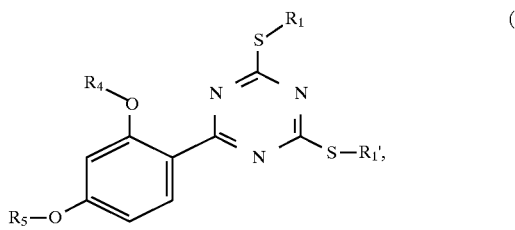

in which $R_1$ und $R_1'$ independently of one another are each linear or branched $C_1$–$C_{18}$alkyl, $C_3$–$C_8$cycloalkyl, $C_3$–$C_6$alkenyl, unsubstituted or substituted aryl or $C_7$–$C_{12}$aralkyl, $R_2$, $R_2'$, $R_3$, $R_3'$, $R_4$ and $R_5$ independently of one another are each hydrogen, unsubstituted or substituted, linear or branched $C_1$–$C_{12}$alkyl, or linear or branched $C_4$–$C_{28}$alkyl, which is interrupted by one or more N, S or O atoms and which may be substituted further or are a radical —CO—$R_6$ or —$SO_2$—$R_6$, and $R_6$ is $C_1$–$C_{12}$alkyl, unsubstituted or $C_1$–$C_4$alkyl-substituted phenyl or $C_7$–$C_{12}$aralkyl.

$R_1$ and $R_1'$ as $C_1$–$C_{18}$alkyl comprise straight-chain or branched alkyl radicals, for example, methyl, ethyl, n- or isopropyl, n-, iso-, sec- or tert-butyl, 2-ethylbutyl, n- or isopentyl, 1-methylpentyl, 1,3-dimethylbutyl, n-hexyl, 1-methylhexyl, n- or isoheptyl, 1,1,3,3-tetra-methylbutyl, 1-methylheptyl, 3-methylheptyl, n-octyl, 2-ethylhexyl, 1,1,3-trimethylhexyl, 1,1,3,3-tetramethylpentyl, nonyl, decyl, undecyl, dodecyl, 1,1,3,3,5,5-hexamethylhexyl, tridecyl, tetradecyl, pentadecyl, hexadecyl, heptadecyl or octadecyl. $R_1$ and $R_1'$ as alkyl, independently of one another, are each preferably $C_1$–$C_6$alkyl, particularly preferably $C_1$–$C_4$alkyl, and with particular preference are each methyl.

$R_1$ and $R_1'$ as a cycloalkyl radical comprise, for example, a saturated 3- to 8-membered carbocyclic ring, which is unsubstituted or substituted by one or more $C_1$–$C_4$alkyl groups, preferably methyl groups. Examples are cyclopentyl, cyclohexyl, methylcyclohexyl or cycloheptyl. As a cycloalkyl radical, $R_1$ and $R_1'$ are preferably and independently of one another each cyclohexyl which is unsubstituted or substituted by 1–3 methyl groups.

Examples of suitable alkenyl radicals $R_1$ or $R_1'$ are allyl, isopropenyl, 2-butenyl, 3-butenyl, isobutenyl, n-penta-2,4-dienyl or 3-methylbut-2-enyl. $R_1$ and $R_1'$ as an alkenyl radical are, independently of one another, each preferably allyl or isopropenyl, and with particular preference are each allyl.

$R_1$ and $R_1'$ as an aryl radical are, for example, a biphenyl, naphthyl, or in particular, a phenyl radical, each of which can be substituted further by, for example, $C_1$–$C_4$alkyl, $C_1$–$C_4$alkoxy or halogen. Preferred definitions of $R_1$ and $R_1'$ as aryl radical are, independently of one another, each unsubstituted or $C_1$–$C_4$alkyl-substituted phenyl, and with particular preference are in each case phenyl.

Examples of suitable aralkyl radicals $R_1$ and $R_1'$ are benzyl, α-methylbenzyl, phenylethyl, phenylpropyl, phenylbutyl, phenylpentyl or phenylhexyl. $R_1$ and $R_1'$ as an aralkyl radical, independently of one another, are each preferably benzyl or α-methylbenzyl, and with particular preference are each benzyl.

The radicals $R_1$ and $R_1'$ can be different or, preferably, identical.

A preferred embodiment of the present invention relates to stabilizer mixtures comprising at least one of each compound of the above formulae (1) and (2) in which $R_1$ and $R_1'$ independently of one another are each $C_1$–$C_6$alkyl, cyclohexyl which is unsubstituted or substituted by 1–3 methyl groups, or are allyl, isopropenyl, unsubstituted or $C_1$–$C_4$alkyl-, $C_1$–$C_4$alkoxy- or halo-substituted phenyl, benzyl or α-methylbenzyl.

A particularly preferred embodiment of the present invention relates to stabilizer mixtures comprising at least one of each compound of the above formulae (1) and (2) in which $R_1$ and $R_1'$ are identical and are each $C_1$–$C_4$alkyl, cyclohexyl, allyl, phenyl or benzyl.

An especially preferred embodiment of the present invention relates to stabilizer mixtures of compounds of the above formulae (1) and (2) in which $R_1$ and $R_1'$ are identical and are each $C_1$–$C_4$alkyl, especially methyl.

Where $R_2$, $R_2'$, $R_3$, $R_3'$, $R_4$ or $R_5$ are $C_1$–$C_{12}$alkyl, this can, for example, be one of the $C_1$–$C_{12}$alkyl radicals mentioned above for $R_1$ or a corresponding $C_1$–$C_{12}$alkyl radical which is substituted, for example, by halogen, cyano, hydroxyl, amino, $C_1$–$C_4$alkoxycarbonyl, carbamoyl, N-mono- or N,N-di-$C_1$–$C_4$alkyl carbamoyl, glycidyl or phenyl. Examples of suitable $C_1$–$C_4$alkoxycarbonyl substituents are methoxycarbonyl or ethoxycarbonyl. Glycidyl is the 2,3-epoxypropyl radical.

$R_2$, $R_2'$, $R_3$, $R_3'$, $R_4$ and $R_5$ as alkyl radical are, independently of one another, each preferably $C_1$–$C_6$alkyl, particularly preferably $C_1$–$C_4$alkyl and with particular preference methyl, ethyl or n- or isopropyl.

Where $R_2$, $R_2'$, $R_3$, $R_3'$, $R_4$ or $R_5$ are an alkyl radical which is interrupted by heteroatoms, then the radical is, for example, straight-chain or branched $C_4$–$C_{28}$alkyl, which is interrupted by one or more groups —O—, —NH— or —S— and which may be substituted further by hydroxyl or by a radical —$OR_6$, in which $R_6$ is as defined above; in such compounds, heteroatom groups —O—, —NH—or —S— that are present do not occur adjacently. $R_2$, $R_2'$, $R_3$, $R_3'$, $R_4$ or $R_5$ as an alkyl radical interrupted by heteroatoms are, preferably and independently of one another, each a straight-chain or branched $C_4$–$C_{28}$alkyl radical which is interrupted by one or more groups —O— and is substituted by hydroxyl or by a radical —$OR_6$. $R_2$, $R_2'$, $R_3$, $R_3'$, $R_4$ and $R_5$ as a heteroalkyl radical are, independently of one another, each preferably of the formula —($CH_2CHR_7$—O)$_n$—$R_8$, in which $R_7$ is hydrogen, methyl or ethyl, $R_8$ is hydrogen, $C_1$–$C_{12}$alkyl or phenyl and n is an integer from 1 to 9, and with particular preference are of the formula —($CH_2CHR_7$—O)$_n$—H, in which $R_7$ is methyl or, in particular, hydrogen and n is an integer from 1 to 9.

Where $R_6$ is a $C_1$–$C_{12}$alkyl radical it may be, for example, one of the $C_1$–$C_{12}$alkyl radicals mentioned above for $R_1$. $R_6$ as an alkyl radical is preferably $C_1$–$C_4$alkyl, particularly preferably methyl or ethyl and, with special preference, methyl. Where $R_6$ is a phenyl radical, it is preferably phenyl, o-, m- or p-tolyl and with particular preference, phenyl. Where $R_6$ is an aralkyl radical, it is preferably benzyl.

$R_2$, $R_2'$, $R_3$, $R_3'$, $R_4$ and $R_5$ are, independently of one another, each preferably hydrogen, $C_1$–$C_6$alkyl or straight-chain or branched $C_4$–$C_{28}$alkyl, which is interrupted by one or more groups —O— and is substituted by hydroxyl or by a radical —$OR_6$, in which $R_6$ is $C_1$–$C_4$alkyl, phenyl, o-, m- or p-tolyl or benzyl, or are unsubstituted or $C_1$–$C_4$alkyl-substituted benzoyl or phenylsulfonyl. Particularly preferred definitions of $R_2$, $R_2'$, $R_3$, $R_3'$, $R_4$ and $R_5$ are, independently of one another, each hydrogen, $C_1$–$C_4$alkyl, a radical of formula —$(CH_2CHR_7—O)_n$—H, in which $R_7$ is methyl or, in particular, hydrogen and n is an integer from 1 to 9, and benzoyl. $R_2$, $R_2'$, $R_3$, $R_3'$, $R_4$ and $R_5$, independently of one another, are with particular preference each hydrogen, methyl, ethyl or n- or isopropyl.

A preferred embodiment of the present invention relates to the stabilizer mixtures comprising at least one of each compound of the above formulae (1) and (2) in which $R_2$, $R_2'$ and $R_5$ independently of one another are each $C_1$–$C_4$alkyl, a radical of the formula —$(CH_2CHR_7—O)_n$—H, in which $R_7$ is methyl or, in particular, hydrogen and n is an integer from 1 to 9, or benzoyl, $R_3$ is hydrogen, $C_1$–$C_4$alkyl, a radical of the formula —$(CH_2CHR_7—O)_n$—H, in which $R_7$ is methyl or, in particular, hydrogen and n is an integer from 1 to 9, or benzoyl, and $R_3'$ and $R_4$ are each hydrogen.

A particularly preferred embodiment of the present invention relates to stabilizer mixtures comprising at least one of each compound of the above formulae (1) and (2), in which $R_2$, $R_2'$ and $R_5$ are identical and are each $C_1$–$C_4$alkyl, $R_3$ is hydrogen or $C_1$–$C_4$alkyl and $R_3'$ and $R_4$ are each hydrogen.

The compounds of the formula (1) are known, for example, from EP-A-0 584 044 or can be prepared by the methods described therein, for example by condensation of 1 mol-equivalent of cyanuric chloride with about 1 mol-equivalent of a compound $R_1$—SH, in which $R_1$ is as defined above and subsequent reaction of the condensation product with two mol-equivalents of the corresponding benzene compound in the presence of a Lewis acid.

Some of the compounds of the formula (2) are novel. The invention additionally provides, therefore, compounds with the above formula (2), in which $R_1$ and $R_1'$ independently of one another are each linear or branched $C_1$–$C_{18}$alkyl, $C_3$–$C_8$cycloalkyl, $C_3$–$C_6$alkenyl or $C_7$–$C_{12}$-aralkyl, $R_4$ and $R_5$ independently of one another are each hydrogen, unsubstituted or substituted, linear or branched $C_1$–$C_{12}$alkyl, linear or branched $C_4$–$C_{28}$alkyl which is interrupted by one or more N, S, or O atoms and which may be substituted further, or are a radical —CO—$R_6$ or —$SO_2$—$R_6$ and, $R_6$ is $C_1$–$C_{12}$alkyl, unsubstituted or $C_1$–$C_4$alkyl-substituted phenyl or $C_7$–$C_{12}$aralkyl.

The compounds of the formula (2) can be prepared in an analogy to the known compounds of the formula (1), for example by reacting 1 mol-equivalent of cyanuric chloride with about 1 mol-equivalent of a compound $R_1$—SH and about 1 mol-equivalent of a compound $R_1'$—SH and, in a subsequent step, reacting the product with about 1 mol-equivalent of the corresponding benzene compound in the presence of a Lewis acid, preferably aluminium chloride, $R_1$ and $R_1'$ each being as defined above and being different or, preferably, identical.

The novel stabilizer mixtures can be obtained by methods known per se from the individual compounds, for example by mixing them or subjecting them to conjoint grinding or cocrystallization. It is also possible to carry out mixing by simultaneous or successive incorporation of the compounds of the formulae (1) and (2) into the textile fibre substrate that is to be stabilized.

The invention also provides the preparation of the novel stabilizer mixtures by conjoint synthesis, which is particularly preferred for those mixtures comprising at least one compound of the above formulae (1) and (2) in which $R_1$ and $R_1'$ are identical. In accordance with this preparation, the novel stabilizer mixtures are prepared, for example, by (i) condensing a cyanuric halide, for example cyanuric fluoride or preferably, cyanuric chloride, in aqueous or aqueous-organic solution with an excess of a compound of the formula

$$R_1—S - X \qquad (3)$$

in which X is hydrogen or a cation and $R_1$ is as defined above, in the presence or absence of a hydrogen halide acceptor, which must be present if X=hydrogen, (ii) reacting the mixture obtainable in accordance with (i), comprising the compounds of the formulae

(4a)

and

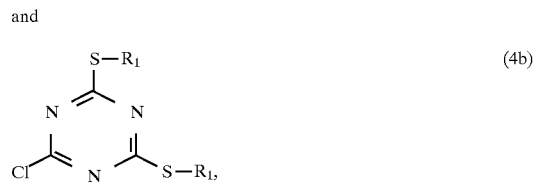

(4b)

with resorcinol in the presence of a Lewis acid, and (iii) converting the mixture obtainable in accordance with (ii), comprising the compounds of the formulae

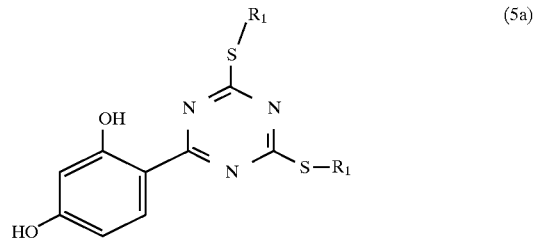

(5a)

and

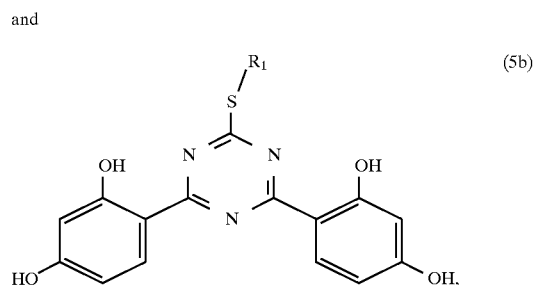

(5b)

with or without one or more acylating or alkylating agents comprising the radicals $R_2$, $R_2'$, $R_3$, $R_3'$, $R_4$ and/or $R_5$, into a novel stabilizer mixture.

The reaction of the compound of the formula (3) with the cyanuric halide in step (i) is known, for example, from GB-A-1,176,770, or can be performed in analogy thereto. The reaction is conducted, for example, at a temperature of from −5° to 100° C. and, preferably, from 0° to 50° C. in a medium comprising water and, if desired, an organic solvent, for example an akylbenzene such as toluene or xylene, a substituted benzene such as chlorobenzene, nitrobenzene or anisole, or an unsubstituted or substituted, aliphatic or cycloaliphatic hydrocarbon such as pentane, hexane, cyclohexane, dibutyl ether, methylene chloride or chloroform. Preferred organic solvents are alkylbenzenes, especially toluene, o-, m- or p-xylene or a mixture of different xylenes. Examples of suitable hydrogen halide acceptors in step (i) are the carbonates, bicarbonates or hydroxides of alkali metals or of alkaline earth metals, and preferably alkali metal hydroxides such as sodium or potassium hydroxide. The addition of a hydrogen halide acceptor is unnecessary if a compound of the formula (3a) is employed in which X is a cation, for example an alkali metal, alkaline earth metal or ammonium cation, and preferably an alkali metal cation such as the potassium or, in particular, the sodium cation. The ratio in which the compounds of the fomulae (4a) and (4b) are obtained in step (i) depends, for example, on the stoichiometric proportion of the reactants used, on the cyanuric halide and on the compound of the formula (3), and can vary, for example, between 95 and 5% by weight of compound of the formula (4a) and between 5 and 95% by weight of compound of the formula (4b).

The reaction with resorcinol of the product obtainable in (i) takes place generally under the customary conditions for Friedel-Crafts reactions, for example at a temperature of from 10° to 50° C. and preferably, from 25° to 40° C. in the presence of a Lewis acid, advantageously aluminium chloride. In this reaction the resorcinol and the Lewis acid are each advantageously present in at least equimolar amounts or, preferably, in a certain molar excess relative to the molar amount of the halogen which is to be replaced on the cyanuric halide. For example, both for the molar ratio of resorcinol/halogen to be replaced, and for the molar ratio of Lewis acid/halogen to be replaced, a value which has been found favourable in each case is from 1:1 to 2:1 and, preferably, from 1.1:1 to 1.5:1.

Steps (i) and (ii) of the novel process can be conducted separately or else as a one-pot reaction. In the case of the preferred embodiment using the one-pot procedure, the organic phase obtained in step (i) is advantageously dried, for example by means of azeotropic distillation, and is reacted further, without additional purification, in accordance with step (ii).

Examples of suitable alkylating agents in the optional step (iii) are alkyl halides R-Hal, in which R is any alkyl radical and Hal is halogen, for example chlorine, bromine or iodine, dialkyl carbonates, for example dimethyl carbonate, mono- or dialkyl sulfates of the general formula R—O—SO$_2$—OH, R—O—SO$_2$—O—R or R—O—SO$_2$—C$_6$H$_5$—CH$_3$, alkyl phosphonates of the formula R—O—P(O)(Z)—O—R, in which each R is any alkyl radical and Z is, for example, C$_1$–C$_4$-alkyl or hydroxyl, or amide acetals, for example dimethylformamide dimethyl acetal. Examples of methylating agents are dimethyl sulfate, methyl tosylate or dimethyl methanephosphonate (DMMP). An ethyl radical R$_2$, R$_2$', R$_3$, R$_3$', R$_4$ or R$_5$ is introduced, for example, using diethyl sulfate. The alkylation reaction is generally carried out at temperatures of, for example, from 10° to 200° C. and, preferably, from 80° to 150° C., in the presence of a base, for example an alkali metal carbonate or alkali metal hydroxide, examples being sodium carbonate, potassium carbonate or sodium hydroxide, with an excess of alkylating agent, the degree of alkylation being influenced, for example, by the stoichiometry and the reaction time. The hydroxyl groups present on the triazinyl ring, in the p position relative to the bond, in the compounds of the formulae (5a) and (5b) are in general more readily accessible than those in the o position and are therefore alkylated first. Examples of suitable acylating agents are compounds of the formula R$_6$—CO—Y or R$_6$—SO$_2$—Y in which R$_6$ is as defined above and Y is halogen, preferably chlorine.

A preferred stabilizer mixture obtained by the novel conjoint and synthesis essentially comprises the compounds of the formula

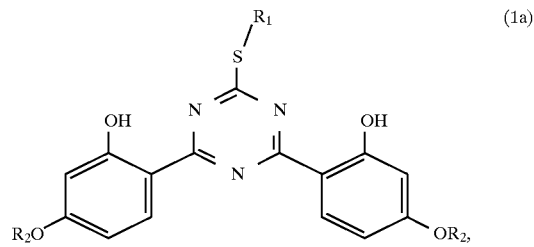

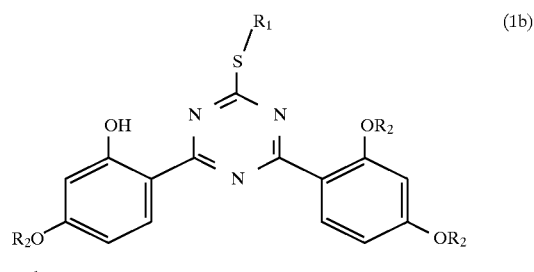

and

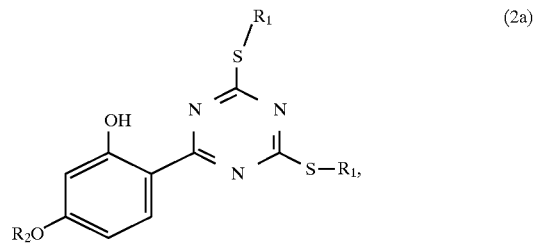

in which R$_1$ and R$_2$ are each subject to the definitions and preferences indicated above. Particularly preferred stabilizer mixtures are those comprising from 50 to 95% by weight of compounds of the above formulae (1 a) and (1 b) and from 50 to 5% by weight of the compound of the above formula (2a).

Especially preferred stabilizer mixtures are those comprising from 50 to 80% by weight of compounds of the above formulae (1 a) and (1 b) and from 50 to 20% by weight of the compounds of the above formula (2a) in which R$_1$ is C$_1$–C$_4$alkyl, cyclohexyl, allyl, phenyl or benzyl and R$_2$ is C$_1$–C$_4$alkyl, a radical of the formula —(CH$_2$CHR$_4$—O)$_n$—H, in which R$_4$ is methyl or in particular, hydrogen and n is an integer from 1 to 9, or benzoyl.

The novel stabilizer mixtures can be used as a stabilizer for organic materials, especially against damage by light, oxygen or heat. The novel compounds and stabilizer mixtures are very particularly suitable as light stabilizers (UV absorbers).

Particular advantages of the novel mixtures include the outstanding resistance of the stabilized material to effects of weathering and light, and the outstanding photostability of the incorporated stabilizer mixtures. The excellent substrate compatibility of the novel mixtures is also deserving of mention. The novel mixtures are notable in particular for high affinity.

The materials to be stabilized can, for example, be oils, fats, waxes, cosmetics or biocides. Of particular interest is their use in polymeric materials as present in plastics, rubbers, coating materials, photographic materials or adhesives. Examples of polymers and other substrates which can be stabilized in this way are the following:

1. Polymers of monoolefins and diolefins, for example polypropylene, polyisobutylene, poly-but-1-ene, poly-4-methylpent-1-ene, polyisoprene or polybutadiene, as well as polymers of cycloolefins, for example of cyclopentene or norbornene; furthermore polyethylene (which optionally can be crosslinked), for example high-density polyethylene (HDPE), high-density and high molecular weight polyethylene (HDPE-HMW), high-density and ultrahigh molecular weight polyethylene (HDPE-UHMW), medium-density polyethylene (MDPE), low-density polyethylene (LDPE), linear low-density polyethylene (LLDPE), branched low-density polyethylene (BLDPE).

Polyolefins, i.e. polymers of monoolefins exemplified in the preceding paragraph, in particular polyethylene and polypropylene, can be prepared by different, and especially by the following, methods:

a) radical polymerization (normally under high pressure and at elevated temperature)

b) catalytic polymerization using a catalyst that normally contains one or more metals of group IVb, Vb, VIb or VIII. These metals usually have one or more ligands, such as oxides, halides, alcoholates, esters, ethers, amines, alkyls, alkenyls and/or aryls that may be either $\pi$- or $\sigma$-coordinated. These metal complexes may be in the free form or fixed on substrates, for example on activated magnesium chloride, titanium(IIII) chloride, alumina or silicon oxide. These catalysts may be soluble or insoluble in the polymerization medium. The catalysts can be active as such in the polymerization or further activators may be used, for example metal alkyls, metal hydrides, metal alkyl halides, metal alkyl oxides or metal alkyloxanes, the metals being elements of groups Ia, Ia and/or IIIa. The activators may be modified, for example, with further ester, ether, amine or silyl ether groups. These catalyst systems are usually termed Phillips, Standard Oil Indiana, Ziegler (-Natta), TNZ (DuPont), metallocene or single site catalysts (SSC).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene-propylene copolymers, linear low density polyethylene (LLDPE) and mixtures thereof with low density polyethylene (LDPE), propylene-but-1-ene copolymers, propylene-isobutylene copolymers, ethylene-but-1-ene copolymers, ethylene-hexene copolymers, ethylene-methylpentene copolymers, ethylene-heptene copolymers, ethylene-octene copolymers, propylene-butadiene copolymers, isobutylene-isoprene copolymers, ethylene-alkyl acrylate copolymers, ethylene-alkyl methacrylate copolymers, ethylene-vinyl acetate copolymers and their copolymers with carbon monoxide or ethylene-acrylic acid copolymers and their salts (ionomers) as well as terpolymers of ethylene with propylene and a diene such as hexadiene, dicyclopentadiene or ethylidene-norbornene; and also mixtures of such copolymers with one another and with polymers mentioned under 1), for example polypropylene-ethylene-propylene copolymers, LDPE-ethylene-vinyl acetate copolymers, LDPE-ethylene-acrylic acid copolymers, LLDPE-ethylene-vinyl acetate copolymers, LLDPE-ethylene-acrylic acid copolymers and alternating or random polyalkylene-carbon monoxide copolymers and mixtures thereof with other polymers, for example polyamides.

4. Hydrocarbon resins (for example $C_5$–$C_9$) including hydrogenated modifications thereof (e.g. tackifier resins) and mixtures of polyalkylenes and starch.

5. Polystyrene, poly(p-methylstyrene), poly($\alpha$-methylstyrene).

6. Copolymers of styrene or $\alpha$-methylstyrene with dienes or acrylic derivatives, for example styrene-butadiene, styrene-acrylonitrile, styrene-alkyl methacrylate, styrene-butadiene-alkyl acrylate, styrene-butadiene-alkyl methacrylate, styrene-maleic anhydride, styrene-acrylonitrile-methyl acrylate; mixtures of high impact strength of styrene copolymers and another polymer, for example a polyacrylate, a diene polymer or an ethylene-propylene-diene terpolymer, and block copolymers of styrene such as styrene-butadiene-styrene, styrene-isoprene-styrene, styrene-ethylene-butylene-styrene or styrene-ethylene-propylene-styrene.

7. Graft copolymers of styrene or $\alpha$-methylstyrene, for example styrene on polybutadiene, styrene on polybutadiene-styrene or polybutadiene-acrylonitrile copolymers, styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene, styrene and alkyl acrylates or alkyl methacrylates on polybutadiene, styrene and acrylonitrile on ethylene-propylene-diene terpolymers, styrene and acrylonitrile on polyalkyl acrylates or polyalkyl methacrylates, styrene and acrylonitrile on acrylate-butadiene copolymers, as well as mixtures thereof with the copolymers mentioned under 6), for example the copolymer mixtures known as ABS, MBS, ASA or AES polymers.

8. Halogen-containing polymers such as polychloroprene, chlorinated rubber, chlorinated and brominated copolymer of isobutylene-isoprene (halobutyl rubber), chlorinated or sulfo-chlorinated polyethylene, copolymers of ethylene and chlorinated ethylene, epichlorohydrin homo- and copolymers, especially polymers of halogen-containing vinyl compounds, for example polyvinyl chloride, polyvinylidene chloride, polyvinyl fluoride, polyvinylidene fluoride; as well as copolymers thereof such as vinyl chloride-vinylidene chloride, vinyl chloride-vinyl acetate or vinylidene chloride-vinyl acetate.

9. Polymers derived from $\alpha,\beta$-unsaturated acids and derivatives thereof such as polyacrylates and polymethacrylates, polymethyl methacrylates, impact-modified with butyl acrylate, polyacrylamides and polyacrylonitriles.

10. Copolymers of the monomers mentioned under 9) with each other or with other unsaturated monomers, for example acrylonitrile-butadiene copolymers, acrylonitrile-alkyl acrylate copolymers, acrylonitrile-alkoxyalkyl acrylate copolymers, acrylonitrile-vinyl halide copolymers or acrylonitrile-alkyl methacrylate-butadiene terpolymers.

11. Polymers derived from unsaturated alcohols and amines or the acyl derivatives or acetals thereof, such as polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in point 1.

12. Homopolymers and copolymers of cyclic ethers such as polyalkylene glycols, polyethylene oxide, polypropylene oxide or copolymers thereof with bisglycidyl ethers.

13. Polyacetals such as polyoxymethylene and those polyoxymethylenes which contain comonomers, for example ethylene oxide; polyacetals modified with thermoplastic polyurethanes, acrylates or MBS.

14. Polyphenylene oxides and sulfides, and mixtures thereof with styrene polymers or polyamides.

15. Polyurethanes derived from hydroxyl-terminated polyethers, polyesters and polybutadienes on the one hand and aliphatic or aromatic polyisocyanates on the other, as well as precursors thereof.

16. Polyamides and copolyamides derived from diamines and dicarboxylic acids and/or from aminocarboxylic acids or the corresponding lactams, such as polyamide 4, 6, 6/6, 6/10, 6/9, 6/12, 4/6, 12/12,11 and 12, aromatic polyamides starting from m-xylene, diamine and adipic acid; polyamides prepared from hexamethylenediamine and isophthalic and/or terephthalic acid and with or without an elastomer as modifier, for example poly-2,4,4-trimethylhexamethylene terephthalamide or poly-m-phenylene isophthalamide. Block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol. Also, polyamides or copolyamides modified with EPDM or ABS; and polyamides condensed during processing (RIM polyamide systems).

17. Polyureas, polyimides, polyamide-imides, polyether imides, polyester imides, polyhydantoins and polybenzimidazoles.

18. Polyesters derived from dicarboxylic acids and dialcohols and/or from hydroxycarboxylic acids or the corresponding lactones, such as polyethylene terephthalate, polybutylene terephthalate, poly-1,4-dimethylolcyclohexane terephthalate, polyhydroxybenzoates, as well as block polyether esters derived from hydroxyl-terminated polyethers; and also polyesters modified with polycarbonates or MBS.

18a. Acid-modified polyesters.

19. Polycarbonates and polyester carbonates.

20. Polysulfones, polyether sulfones and polyether ketones.

21. Crosslinked polymers derived from aldehydes on the one hand and phenols, urea or melamine on the other hand, such as phenol-formaldehyde resins, urea-formaldehyde resins and melamine-formaldehyde resins.

22. Drying and nondrying alkyd resins.

23. Unsaturated polyester resins derived from copolyesters of saturated and unsaturated di-carboxylic acids with polyhydric alcohols and also vinyl compounds as crosslinking agents, and also halogen-containing modifications thereof of low flammability.

24. Crosslinkable acrylic resins derived from substituted acrylates, for example from epoxy acrylates, urethane acrylates or polyester acrylates.

25. Alkyd resins, polyester resins and acrylate resins crosslinked with melamine resins, urea resins, isocyanates, isocyanurates, polyisocyanates or epoxy resins.

26. Crosslinked epoxy resins derived from aliphatic, cycloaliphatic, heterocyclic or aromatic glycidyl compounds, for example products of bisphenol A diglycidyl ethers, bisphenol F diglycidyl ethers, which are crosslinked by means of customary curing agents such an anhydrides or amines, with or without accelerators.

27. Natural polymers such as cellulose, natural rubber, gelatin and derivatives thereof which have been chemically modified in a polymer-homologous manner, for example cellulose acetates, cellulose propionates and cellulose butyrates, or the cellulose ethers such as methyl cellulose; as well as rosins and derivatives.

28. Blends (polyblends) of the aforementioned polymers, for example PP/EPDM, polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PU, PC/thermoplastic PU, POM/acrylate, POM/MBS, PPO/HIPS, PPO/PA 6.6 and copolymers, PA/HDPE, PA/PP, PA/PPO, PBT/PC/ABS or PBT/PET/PC.

In addition to the novel mixture of compounds, the novel compositions may also comprise other stabilizers or other additives, such as antioxidants, other light stabilizers, metal deactivators, phosphites or phosphonites. Examples of these are the following stabilizers:

1. Antioxidants 1.1. Alkylated monophenols, for example 2,6-di-tert-butyl-4-methylphenol, 2-tert-butyl-4,6-di-methylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, nonylphenols which are linear or branched in the side chains, for example, 2,6-di-nonyl-4-methylphenol, 2,4-dimethyl-6-(1'-methylundec-1'-yl) phenol, 2,4-dimethyl-6-(1'-methylheptadec-1'-yl)phenol, 2,4-dimethyl-6-(1'-methyltridec-1'-yl)phenol and mixtures thereof.

1.2. Alkylthiomethylphenols, for example 2,4-dioctylthiomethyl-6-tert-butylphenol, 2,4-dioctylthiomethyl-6-methylphenol, 2,4-dioctylthiomethyl-6-ethylphenol, 2,6-di-dodecylthiomethyl-4-nonylphenol.

1.3. Hydroquinones and alkylated hydroquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis-(3,5-di-tert-butyl-4-hydroxyphenyl) adipate.

1.4. Tocopherols, for example α-tocopherol, β-tocopherol, γ-tocopherol, δ-tocopherol and mixtures thereof (Vitamin E).

1.5. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl- 2-methylphenol), 4,4'-thiobis-(3, 6-di-sec-amylphenol), 4,4'-bis(2,6-dimethyl-4-hydroxyphenyl)disulfide.

1.6. Alkylidenebisphenols, for example 2,2'-methylenebis (6-tert-butyl-4-methylphenol), 2,2'-methylenebis(6-tert-butyl-4-ethylphenol), 2,2'-methylenebis[4-methyl-6-(α-methylcyclohexyl)-phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(α-methylbenzyl)-4-nonylphenol], 2,2'-methylenebis[6-(α,β-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl) butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methyl-phenyl)-3-n-dodecylmercaptobutane, ethylene glycol bis[3,3-bis(3'-tert-butyl-4'-hydroxyphenyl)butyrate], bis(3-tert-butyl-4- hydroxy-5-methyl-phenyl)dicyclopentadiene, bis[2-(3'-tert-butyl-2'-hydroxy-5'-methylbenzyl)-6-tert-butyl-4-methylphenyl]terephthalate, 1,1 -bis-(3,5-dimethyl-2-hydroxyphenyl)butane, 2,2-bis-(3,5-di-tert-butyl-4-hydroxyphenyl)propane, 2,2-bis-(5-tert-butyl-4-hydroxy2-methylphenyl)-4-n-dodecylmercaptobutane, 1,1,5,5-tetra-(5-tert-butyl-4-hydroxy-2-methylphenyl) pentane.

1.7. O—, N— and S-benzyl compounds, for example 3,5, 3',5'-tetra-tert-butyl-4,4'-dihydroxydibenzyl ether, octadecyl-4-hydroxy-3,5-dimethylbenzylmercaptoacetate, tridecyl-4-hydroxy-3,5-di-tert-butylbenzylmercaptoacetate, tris(3,5-di-tert-butyl-4-hydroxybenzyl)amine, bis(4-tert-butyl-3-hydroxy-2,6-dimethylbenzyl)dithioterephthalate, bis(3,5-di-tert-butyl-4-hydroxy-benzyl)sulfide, isooctyl-3,5-di-tert-butyl-4-hydroxybenzylmercaptoacetate.

1.8. Hydroxybenzylated malonates, for example dioctadecyl-2,2-bis-(3,5-di-tert-butyl-2-hydroxybenzyl)-malonate, di-octadecyl-2-(3-tert-butyl-4-hydroxy-5-methylbenzyl)-malonate, di-dodecylmercaptoethyl-2,2-bis-(3,5-di-tert-butyl-4-hydroxybenzyl) malonate, bis[4-(1,1,3,3-tetramethylbutyl)phenyl]-2,2-bis(3,5-di-tert-butyl-4-hydroxybenzyl) malonate.

1.9. Aromatic hydroxybenzyl compounds, for example 1,3, 5-tris-(3,5-di-tert-butyl-4-hydroxybenzyl)-2,4,6-trimethylbenzene, 1,4-bis(3,5-di-tert-butyl-4-hydroxybenzyl)-2,3,5,6-tetramethylbenzene, 2,4,6-tris(3,5-di-tert-butyl-4-hydroxybenzyl) phenol.

1.10. Triazine Compounds, for example 2,4-bis (octylmercapto)-6-(3,5-di-tert-butyl-4-hydroxyanilino)-1,3,5-triazine, 2-octylmercapto-4,6-bis(3,5-di-tert-butyl-4-hydroxyanilino)-1,3,5-triazine, 2-octyl mercapto-4, 6-bis (3,5-di-tert-butyl-4-hydroxyphenoxy)-1,3,5-triazine, 2,4,6-tris(3,5-di-tert-butyl-4-hydroxyphenoxy)-1,2,3-triazine, 1,3,5-tris-(3,5-di-tert-butyl-4-hydroxybenzyl) isocyanu rate, 1,3,5-tris(4-tert-butyl-3-hydroxy-2,6-dimethylbenzyl)isocyanurate, 2,4,6-tris(3,5-di-tert-butyl-4-hydroxyphenylethyl)-1,3,5-triazine, 1,3,5-tris(3,5-di-tert-butyl-4-hydroxyphenylpropionyl)-hexahydro-1,3,5-triazine, 1,3,5-tris(3,5-dicyclohexyl-4-hydroxybenzyl) isocyanurate.

11 1. Benzylphosphonates, for example dimethyl-2,5-di-tert-butyl-4-hydroxybenzylphosphonate, diethyl-3,5-di-tert-butyl-4-hydroxybenzylphosphonate, dioctadecyl3,5-di-tert-butyl-4-hydroxybenzylphosphonate, dioctadecyl-5-tert-butyl-4-hydroxy-3-methylbenzylphosphonate, the calcium salt of the monoethyl ester of 3,5-di-tert-butyl-4-hydroxybenzylphosphonic acid.

1.12. Acylaminophenols, for example 4-hydroxylauranilide, 4-hydroxystearanilide, octyl N-(3,5-di-tert-butyl-4-hydroxyphenyl)carbamate.

1.13. Esters of β(3,5-di-tert-butyl-4-hydroxyphenyl) propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl) oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.14. Esters of β-(5-tert-butyl-4-hydroxy-3-methylphenyl) propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl) oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.15. Esters of β-(3,5-dicyclohexyl-4-hydroxyphenyl) propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanu rate, N, N'-bis(hydroxyethyl) oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.16. Esters of 3,5-di-tert-butyl-4-hydroxyphenyl acetic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.17. Amides of β-(3,5-di-tert-butyl-4-hydroxyphenyl) propionic acid e.g. N,N'-bis(3,5-di-tert-butyl-4-hydroxyphenylpropionyl)hexamethylenediamide, N,N'-bis(3,5-di-tert-butyl-4-hydroxyphenyl propionyl) trimethylenediamide, N,N'-bis(3,5-di-tert-butyl-4-hydroxyphenylpropionyl)-hydrazide, N,N'-bis[2-(3-[3,5-di-tert-butyl-4-hydroxyphenyl]propionyloxy)ethyl] oxamide (Naugard®XL-1 supplied by Uniroyal).

1.18. Ascorbic acid (vitamin C)

1.19. Aminic antioxidants, for example N,N'-di-isopropyl-p-phenylenediamine, N,N'-di-sec-butyl-p-phenylenediamine, N,N'-bis(1,4-dimethylpentyl)-p-phenylenediamine, N,N'-bis(1-ethyl-3-methylpentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-bis(2-naphthyl)-p-phenylenediamine, N-isopropyl-N'-phenyl-p-phenylenediamine, N-(1,3-dimethylbutyl)-N'-phenyl-p-phenylenediamine, N-(1-methyl heptyl)-N'-phenyl-p-phenylenediamine, N-cyclo-hexyl-N'-phenyl-p-phenlenediamine, 4-(p-toluenesulfamoyl)diphenylamine, N,N'-dimethyl-N,N'-di-sec-butyl-p-phenylenediamine, diphenylamine, N-allyldiphenylamine, 4-isopropoxy-diphenylamine, N-phenyl-1-naphthylamine, N-(4-tert-octylphenyl)-1-naphthylamine, N-phenyl-2-naphthylamine, octylated diphenylamine, for example p,p'-di-tert-octyldiphenylamine, 4-n-butylaminophenol, 4-butyrylaminophenol, 4-nonanoylaminophenol, 4-dodecanoylaminophenol, 4-octadecanoylaminophenol, bis(4-methoxyphenyl)amine, 2,6-di-tert-butyl-4-dimethylaminomethylphenol, 2,4'-diaminodiphenylmethane, 4,4'-diaminodiphenylmethane, N,N,N',N'-tetramethyl-4,4'-diaminodiphenylmethane, 1,2-bis[(2-methylphenyl)amino]ethane, 1,2-bis(phenylamino)propane, (o-tolyl)biguanide, bis[4-(1',3'-dimethylbutyl)phenyl]amine, tert-octylated N-phenyl-1-naphthylamine, a mixture of mono- and dialkylated tert-butyl/tertoctyldiphenylamines, a mixture of mono- and dialkylated nonyidiphenylamines, a mixture of mono- and dialkylated dodecyidiphenylamines, a mixture of mono- and dialkylated isopropyl/isohexyldiphenylamines, a mixture of mono- und dialkylated tert-butyldiphenylamines, 2,3-dihydro-3,3-dimethyl-4H-1,4-benzothiazine, phenothiazine, a mixture of mono- und dialkylated tert-butylltert-octylphenothiazines, a mixture of mono- und dialkylated tert-octyl-phenothiazines, N-allylphenothiazin, N,N,N',N'-tetraphenyl-1,4-diaminobut-2-ene, N,N-bis-(2,2,6,6-tetramethyl-piperid-4-yl-hexamethylenediamine, bis(2,2,6,6-tetramethylpiperid-4-yl)sebacate, 2,2,6,6-tetramethylpiperidin-4-one, 2,2,6,6-tetramethylpiperidin-4-ol.

2. UV absorbers and light stabilisers 2.1. 2-(2'-Hydroxyphenyl)benzotriazoles, for example 2-(2'-hydroxy-5'-methylphenyl)-benzo-triazole, 2-(3',5'-di-tert-butyl-2'-hydroxyphenyl)benzotriazole, 2-(5'-tert-butyl-2'-hydroxyphenyl)benzotriazole, 2-(2'-hydroxy-5'-(1,1,3,3-tetramethylbutyl)phenyl)benzotriazole, 2-(3',5'-di-tert-butyl-2'-hydroxyphenyl)-5-chloro-benzotriazole, 2-(3'-tert-butyl-2'-hydroxy-5'-methylphenyl)-5-chloro-benzotriazole, 2-(3'-sec-butyl-5'-tert-butyl-2'-hydroxyphenyl)benzotriazole, 2-(2'-hydroxy-4'-octyloxyphenyl) benzotriazole, 2-(3',5'-di-tert-amyl-2'-hydroxyphenyl)benzotriazole, 2-(3',5'-bis-(α,α-dimethylbenzyl)-2'-hydroxyphenyl)benzotriazole, 2-(3'-tert-butyl-2'-hydroxy-5'-(2-octyloxycarbonylethyl) phenyl)-5-chloro-benzotriazole, 2-(3'-tert-butyl-5'-[2-(2-ethylhexyloxy)-carbonylethyl]-2'-hydroxyphenyl)-5-chloro-benzotriazole, 2-(3'-tert-butyl-2'-hydroxy-5'-(2-methoxycarbonylethyl)phenyl)-5-chloro-benzotriazole, 2-(3'-tert-butyl-2'-hydroxy-5'-(2-methoxycarbonylethyl) phenyl)benzotriazole, 2-(3'-tert-butyl-2'-hydroxy-5'-(2-octyloxy-carbonylethyl)phenyl)benzotriazole, 2-(3'-tert-butyl-5'-[2-(2-ethylhexyloxy)carbonylethyl]-2'-hydroxyphenyl)benzotriazole, 2-(3'-dodecyl-2'-hydroxy-5'-methylphenyl)benzotriazole, 2-(3'-tert-butyl-2'-hydroxy-5'-(2-isooctyloxycarbonylethyl) phenylbenzotriazole, 2,2'-methylene-bis-[4-(1,1,3,3-tetramethylbutyl)-6-benzotriazole-2-ylphenol]; the transesterification product of 2-[3'-tert-butyl-5'-(2-methoxycarbonylethyl)-2'-hydroxyphenyl]-2H-benzotriazole with polyethylene glycol 300; [R—CH$_2$CH$_2$—COO—CH$_2$CH$_2$—]$_2$ where R=3'-tert-butyl-4'-hydroxy-5'-2H-benzotriazol-2-ylphenyl, 2-[2'-hydroxy-3'-(α,α-dimethylbenzyl)-5'-(1,1,3,3-tetramethylbutyl)-phenyl]benzotriazole; 2-[2'-hydroxy-3'-(1,1,3,3-tetramethylbutyl)-5'-(α,α-dimethylbenzyl)-phenyl]benzotriazole.

2.2. 2-Hydroxybenzophenones, for example the 4-hydroxy, 4-methoxy, 4-octyloxy, 4-decyloxy, 4-dodecyloxy, 4-benzyloxy, 4,2',4'-trihydroxy and 2'-hydroxy-4,4'-dimethoxy derivatives.

2.3. Esters of substituted and unsubstituted benzoic acids, as for example 4-tertbutyl-phenyl salicylate, phenyl salicylate, octylphenyl salicylate, dibenzoyl resorcinol, bis(4-tert-butylbenzoyl) resorcinol, benzoyl resorcinol, 2,4-di-tert-butylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate.

2.4. Acrylates, for example ethyl α-cyano-β,β-diphenylacrylate, isooctyl α-cyano-β,β-diphenylacrylate, methyl α-carbomethoxycinnamate, methyl α-cyano-β-methyl-p-methoxy-cinnamate, butyl α-cyano-β-methyl-p-methoxy-cinnamate, methyl α-carbomethoxy-p-methoxycinnamate and N-(β-carbomethoxy-β-cyanovinyl)-2-methylindoline.

2.5. Nickel compounds, for example nickel complexes of 2,2'-thio-bis-[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyldithiocarbamate, nickel salts of the monoalkyl esters, e.g. the methyl or ethyl ester, of 4-hydroxy-3,5-di-tert-butylbenzylphosphonic acid, nickel complexes of ketoximes, e.g. of 2-hydroxy-4-methylphenyl undecylketoxime, nickel complexes of 1-phenyl-4-lauroyl-5-hydroxypyrazole, with or without additional ligands.

2.6. Sterically hindered amines, for example bis(2,2,6,6-tetramethyl-4-piperidyl)sebacate, bis(2,2,6,6-tetramethyl-4-piperidyl)succinate, bis(1,2,2,6,6-pentamethyl-4-piperidyl)sebacate, bis(1-octyloxy-2,2,6,6-tetramethyl-4-piperidyl)sebacate, bis(1,2,2,6,6-pentamethyl-4-piperidyl) n-butyl-3,5-di-tert-butyl-4-hydroxybenzylmalonate, the condensate of 1-(2-hydroxy-ethyl)-2,2,6,6-tetramethyl-4-hydroxypiperidine and succinic acid, linear or cyclic condensates of N,N'-bis(2,2,6,6-tetramethyl-4-piperidyl)hexamethylenediamine and 4-tert-octylamino-2,6-dichloro-1,3,5-triazine, tris(2,2,6,6-tetramethyl-4-piperidyl)nitrilotriacetate, tetrakis-(2,2,6,6-tetramethyl-4-piperidyl)-1,2,3,4-butane-tetracarboxylate, 1,1'-(1,2-ethanediyl)-bis-(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert-butyl benzyl)malonate, 3-n-octyl-7,7,9,9-tetramethyl-1,3,8-triazaspiro[4.5]decan-2,4-dione, bis(1-octyloxy-2,2,6,6-tetramethyl piperidyl)sebacate, bis(1-octyloxy-2,2,6,6-tetramethylpiperidyl)succinate, linear or cyclic condensates of N,N'-bis-(2,2,6,6-tetramethyl-4-piperidyl)hexamethylenediamine and 4-morpholino-2,6-dichloro-1,3,5-triazine, the condensate of 2-chloro-4,6-bis(4-n-butylamino-2,2,6,6-tetramethylpiperidyl )-1,3,5-triazine and 1,2-bis(3-aminopropylamino)ethane, the condensate of 2-chloro-4,6-di-(4-n-butylamino-1,2,2,6,6-pentamethylpiperidyl)-1,3,5-triazine and 1,2-bis-(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl)pyrrolidin-2,5-dione, 3-dodecyl-1-(1,2,2,6,6-pentamethyl-4-piperidyl)pyrrolidine-2,5-dione, a mixture of 4-hexadecyloxy- and 4-stearyloxy-2,2,6,6-tetramethylpiperidine, a condensation product of N,N'-bis (2,2,6,6-tetramethyl-4-piperidyl)hexamethylenediamine and 4-cyclohexylamino-2,6-dichloro-1,3,5-triazine, a condensation product of 1,2-bis(3-aminopropylamino) ethane and 2,4,6-trichloro-1,3,5-triazine as well as 4-butylamino-2,2,6,6-tetramethylpiperidine (CAS Reg. No. [136504-96-6]); N-(2,2,6,6-tetramethyl-4-piperidyl)-n-dodecylsuccinimid, N-(1,2,2,6,6-pentamethyl-4-piperidyl)-n-dodecylsuccinimid, 2-undecyl-7,7,9,9-tetramethyl-1-oxa-3,8-diaza-4-oxo-spiro[4,5]decane, a reaction product of 7,7,9,9-tetramethyl-2-cycloundecyl-1-oxa-3,8-diaza-4-oxospiro [4,5]decane und epichlorohydrin, 1,1-bis(1,2,2,6,6-pentamethyl-4-piperidyloxycarbonyl)-2-(4-methoxyphenyl)ethene, N,N'-bis-formyl-N,N'-bis(2,2,6,6-tetramethyl-4-piperidyl)hexamethylenediamine, diester of 4-methoxy-methylene-malonic acid with 1,2,2,6,6-pentamethyl-4- hydroxypiperidine, poly[methylpropyl-3-oxy-4-(2,2,6,6-tetramethyl-4-piperidyl)]siloxane, reaction product of maleic acid anhydride-α-olefin-copolymer with 2,2,6,6-tetramethyl-4-aminopiperidine or 1,2,2,6,6-pentamethyl-4-aminopiperidine.

2.7. Oxamides, for example 4,4'-dioctyloxyoxanilide, 2,2'-diethoxyoxanilide, 2,2'-dioctyloxy-5,5'-di-tert-butoxanilide, 2,2'-didodecyloxy-5,5'-di-tert-butoxanilide, 2-ethoxy-2'-ethyloxanilide, N,N'-bis(3-dimethylaminopropyl)oxamide, 2-ethoxy-5-tert-butyl-2'-ethoxanilide and its mixture with 2-ethoxy-2'-ethyl-5,4'-di-tert-butoxanilide, mixtures of o- and p-methoxy-disubstituted oxanilides and mixtures of o- and p-ethoxy-disubstituted oxanilides.

2.8. 2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-(2-hydroxy-4-tridecyloxyphenyl)-4,6-bis(2,4-dimethylphenyl)-1,3,5-triazine, 2-[2-hydroxy-4-(2-hydroxy-3-butyloxy-propoxy)phenyl]-4,6-bis(2,4-dimethyl)-1,3,5-triazine, 2-[2-hydroxy-4-(2-hydroxy-3-octyloxy-propyloxy) phenyl]-4,6-bis(2,4-dimethyl)-1,3,5-triazine, 2-[4-(dodecyloxy/tridecyloxy-2-hydroxypropoxy)-2-hydroxy-phenyl]-4,6-bis(2,4-dimethylphenyl)-1,3,5-triazine, 2-[2-hydroxy-4-(2-hydroxy-3-dodecyloxy-propoxy)phenyl]-4,6-bis(2,4-dimethylphenyl)-1,3,5-triazine, 2-(2-hydroxy-4-hexyloxy)phenyl-4,6-diphenyl-1,3,5-triazine, 2-(2-hydroxy-4-methoxyphenyl)-4,6-diphenyl-1,3,5-triazine, 2,4,6-tris[2-hydroxy-4-(3-butoxy-2-hydroxy-propoxy)phenyl]-1,3,5-triazine, 2-(2-hydroxyphenyl)-4-(4-methoxyphenyl)-6-phenyl-1,3,5-triazine, 2-{2-hydroxy-4-[3-(2-ethylhexyl-1-oxy)-2-hydroxypropyloxy]phenyl}-4,6-bis(2,4-dimethylphenyl)-1,3,5-triazine.

3. Metal deactivators, for example N,N'-diphenyloxamide, N-salicylal-N'-salicyloyl hydrazine, N,N'-bis(salicyloyl) hydrazine, N,N'-bis(3,5-di-tert-butyl-4-hydroxyphenylpropionyl) hydrazine, 3-salicyloylamino-1,2,4-triazole, bis(benzylidene)oxalyl dihydrazide, oxanilide, isophthaloyl dihydrazide, sebacoyl bisphenylhydrazide, N,N'-diacetyladipoyl dihydrazide, N,N'-bis(salicyloyl)oxalyl dihydrazide, N,N'-bis(salicyloyl)thiopropionyl dihydrazide.

4. Phosphites and phosphonites, for example triphenyl phosphite, diphenyl alkyl phosphites, phenyl dialkyl phosphites, tris(nonylphenyl) phosphite, trilauryl phosphite, trioctadecyl phosphite, distearyl pentaerythritol diphosphite, tris(2,4-di-tert-butylphenyl) phosphite, diisodecyl pentaerythritol diphosphite, bis(2,4-di-tert-butylphenyl) pentaerythritol diphosphite, bis(2,6-di-tert-butyl-4-methylphenyl)-pentaerythritol diphosphite, diisodecyloxypentaerythritol diphosphite, bis(2,4-di-tert-butyl-6-methyl phenyl)pentaerythritol diphosphite, bis(2,4,6-tris(tert-butylphenyl)pentaerythritol diphosphite, tristearyl sorbitol triphosphite, tetrakis(2,4-di-tert-butylphenyl) 4,4'-biphenylene diphosphonite, 6-isooctyloxy-2,4,8,10-tetra-tert-butyl-12H-di-benz[d,g]-1,3,2-dioxaphosphocin, 6-fluoro-2,4,8,10-tetra-tert-butyl-1 2-methyl-dibenz[d,g]-1,3,2-dioxaphosphocin, bis (2,4-di-tert-butyl-6-methylphenyl) methyl phosphite, bis (2,4-di-tert-butyl-6-methylphenyl) ethyl phosphite, 2,2',2"-nitrilo[triethyltris(3,3',5,5'-tetra-tert-butyl- 1,1'-biphenyl-2,2'-diyl)phosphite], 2-ethylhexyl(3,3',5,5'-tetra-tert-butyl-1,1'-biphenyl-2,2'-di-yl)phosphites:

Expecially preferred are the following phosphites:
Tris(2,4-di-tert-butylphenyl) phosphite (Irgafos®168, Ciba-Geigy), tris(nonylphenyl) phoshite,

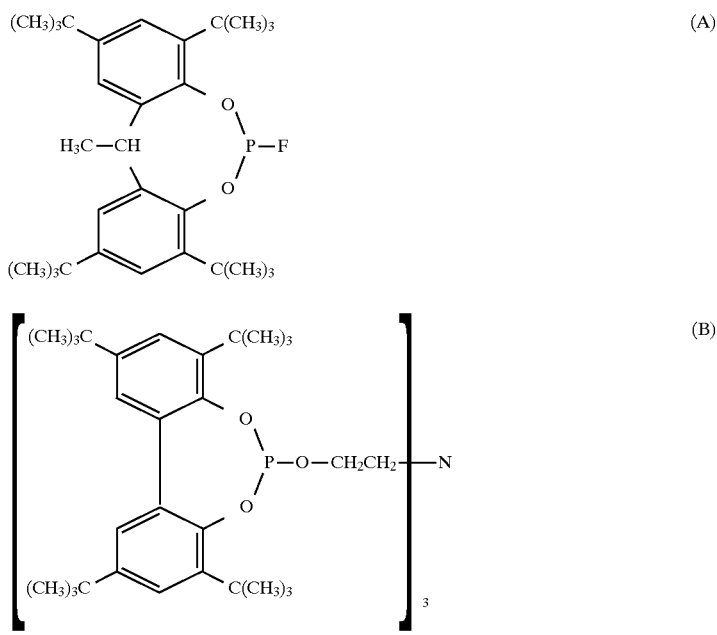

-continued

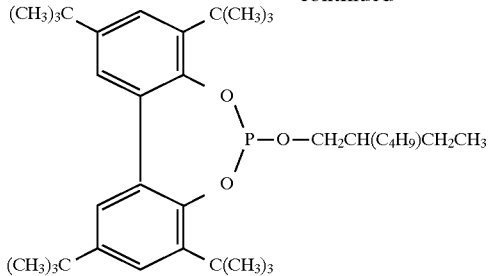
(C)

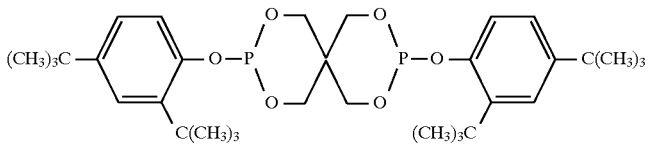
(D)

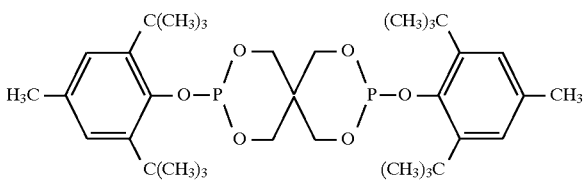
(E)

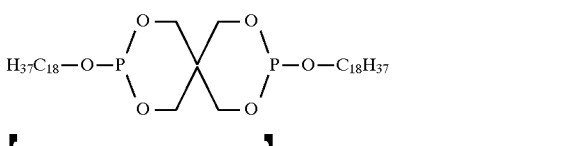
(F)

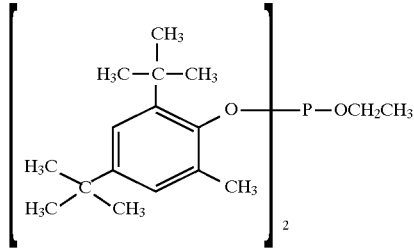
(G)

5. Hydroxylamines, for example, N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N,N-dialkylhydroxylamine derived from hydrogenated tallow amine.

6. Nitrones, for example, N-benzyl-alpha-phenyl-nitrone, N-ethyl-alpha-methyl-nitrone, N-octyl-alpha-heptyl-nitrone, N-lauryl-alpha-undecyl-nitrone, N-tetradecyl-alpha-tridcyl-nitrone, N-hexadecyl-alpha-pentadecyl-nitrone, N-octadecyl-alpha-heptadecyl-nitrone, N-hexadecyl-alpha-heptadecyl-nitrone, N-ocatadecyl-alpha-pentadecyl-nitrone, N-heptadecyl-alpha-heptadecyl-nitrone, N-octadecyl-alpha-hexadecyl-nitrone, nitrone derived from N,N-dialkylhy-droxylamine derived from hydrogenated tallow amine.

7. Thiosynergists, for example, dilauryl thiodipropionate or distearyl thiodipropionate.

8. Peroxide scavengers, for example esters of β-thiodipropionic acid, for example the lauryl, stearyl, myristyl or tridecyl esters, mercaptobenzimidazole or the zinc salt of 2-mercapto-benzimidazole, zinc dibutyldithiocarbamate, dioctadecyl disulfide, pentaerythritol tetrakis(β-dodecylmercapto)propionate.

9. Polyamide stabilisers, for example, copper salts in combination with iodides and/or phosphorus compounds and salts of divalent manganese.

10. Basic co-stabilisers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example calcium stearate, zinc stearate, magnesium behenate, magnesium stearate, sodium ricinoleate and potassium palmitate, antimony pyrocatecholate or zink pyrocatecholate.

11. Nucleating agents, for example, inorganic substances such as talcum, metal oxides such as titanium dioxide or magnesium oxide, phosphates, carbonates or sulfates of, preferably, alkaline earth metals; organic compounds such as mono- or polycarboxylic acids and the salts thereof, e.g. 4-tert-butylbenzoic acid, adipic acid, diphenylacetic acid, sodium succinate or sodium benzoate; polymeric compounds such as ionic copolymers (ionomers).

12. Fillers and reinforcing agents, for example, calcium carbonate, silicates, glass fibres, glass bulbs, asbestos, talc, kaolin, mica, barium sulfate, metal oxides and hydroxides, carbon black, graphite, wood flour and flours or fibers of other natural products, synthetic fibers.

13. Other additives, for example, plasticisers, lubricants, emulsifiers, pigments, rheology additives, catalysts, flow-control agents, optical brighteners, flameproofing agents, antistatic agents and blowing agents.

14. Benzofuranones and indolinones, for example those disclosed in U.S. Pat. No. 4,325,863; U.S. Pat. No. 4,338,244; U.S. Pat. No. 5,175,312; U.S. Pat. No. 5,216,052; U.S.

Pat. No. 5,252,643; DE-A-4316611; DE-A-4316622; DE-A-4316876; EP-A-0589839 or EP-A-0591102 or 3-[4-(2-acetoxyethoxy)-phenyl]-5,7-di-tert-butyl-benzofuran-2-one, 5,7-di-tert-butyl-3-[4-(2-stearoyloxyethoxy)phenyl] benzofuran-2-one, 3,3'-bis[5,7-di-tert-butyl-3-(4-[2-hydroxyethoxy]phenyl) benzofuran-2-one], 5,7-di-tert-butyl-3-(4-ethoxyphenyl)benzofuran-2-one, 3-(4-acetoxy-3, 5-dimethylphenyl)-5,7-di-tert-butyl-benzofuran-2-one, 3-(3, 5-dimethyl-4-pivaloyloxyphenyl)-5,7-di-tert-butyl-benzofuran-2-one, 3-(3,4-dimethylphenyl)-5,7-di-tert-butyl-benzofuran-2-one, 3-(2,3-dimethylphenyl)-5,7-di-tert-butyl-benzofuran-2-one.

The novel stabilizer mixtures are especially suitable for the photochemical and thermal stabilization of undyed, dyed or printed textile fibre materials, which is also provided by the present invention. A corresponding process comprises treating the textile fibre material with a stabilizer mixture comprising at least one compound of the above formula (1) and at least one compound of the above formula (2).

Textile fibre materials suitable for treatment are primarily fibre materials containing polyester or cellulose acetate. The term polyester fibres should be understood as referring, for example, to cellulose ester fibres, such as secondary cellulose acetate fibres and triacetate fibres, and especially linear polyester fibres which may have been acid-modified, such fibres being obtained, for example, by condensation of terephthalic acid with ethylene glycol or of isophthalic acid or terephthalic acid with 1,4-bis(hydroxymethyl) cyclohexane, and also fibres of copolymers of terephthalic and isophthalic acid with ethylene glycol. Customary polyester fibres in the textile fibre industry consist, in particular, of terephthalic acid and ethylene glycol.

The textile fibre material to be treated may also be a blend fabric of polyester fibres and other fibres, examples being blends of polyacrylonitrile/polyester, polyamide/polyester, polyester/cotton, polyester/viscose or polyester/wool fibres, which a reprinted or dyed in a customary, batch or continuous procedure.

The textile fibre material may be in a variety of made-up forms, for example as piece goods such a knits or wovens, or as a yarn on, for example, cheeses, warp beams, etc.

Also highly suitable for the novel process are textile fabrics in the apparel sector which are at least partially light-permeable. Where such textiles are treated in accordance with the novel process, it is possible thereby to protect the skin tissue below the item of apparel against the damaging effect of UV radiation. This is manifested in the fact that textile fibre materials treated with a novel stabilizer or stabilizer mixture can have a sun protection factor (UPF= Ultraviolet Protection Factor) which is markedly increased relative to that of untreated fabric.

The UPF is defined as the ratio formed from a harmful dose of UV radiation without sun protection and a harmful dose of UV radiation with sun protection. Accordingly, a UPF is also a measure of the permeability of the untreated fibre materials and of the fibre materials treated with a novel compound or a novel mixture of compounds to UV radiation. Determining the UPF of textile fibre materials is explained, for example, in WO 94/04515 or in J. Soc. Cosmet. Chem. 40, pages 127–133 (1989) and can be carried out analogously.

The novel stabilizer mixtures are employed in an amount of, for example, from 0.01 to 10% by weight, preferably from 0.1 to 5 % by weight, based on the weight on the fibre material.

The novel stabilizer mixtures are of low solubility in water and are therefore applied in dispersed form. For this purpose they are ground to a fineness in accordance with the application conditions using, for example, an appropriate dispersant and with the aid of, for example, quartz beads and a high-speed stirrer.

Examples of suitable dispersants for the stabilizer mixtures are:

acidic esters or their salts of alkylene oxide adducts, for example acidic esters or their salts of a polyadduct of from 4 to 40 mol of ethylene oxide with 1 mol of a phenol, or phosphoric esters of the adducts of from 6 to 30 mol of ethylene oxide with 1 mol of 4-nonylphenol, 1 mol of dinonylphenol or, in particular, with 1 mol of compounds which are prepared by adding from 1 to 3 mol of substituted or unsubstituted styrenes onto 1 mol of phenol, polystyrenesulfonates, fatty acid taurides, alkylated diphenyl oxide mono- or di-sulfonates, sulfonates of polycarboxylic esters, adducts of from 1 to 60, preferably 2 to 30 mol of ethylene oxide and/or propylene oxide with fatty amines, fatty amides, fatty acids or fatty alcohols each having from 8 to 22 carbon atoms, or with trihydric to hexahydric alkanols of 3 to 6 carbon atoms, which adducts are converted into an acidic ester using an organic dicarboxylic acid or an inorganic polybasic acid, ligninsulfonates, and very especially formaldehyde condensates, for examples condensates of ligninsulfonates and/or phenol and formaldehyde, condensates of formaldehyde with aromatic sulfonic acids, such as condensates of ditolyl ether sulfonates and formaldehyde, condensates of naphthalene sulfonic and/or naphthol- or naphthylamine sulfonic acids with formaldehyde, condensates of phenolsulfonic acids and/or sulfonated dihydroxy-diphenyl sulfone and phenols and/or cresols with formaldehyde and/or urea, and condensates of diphenyl oxide disulfonic acid derivatives with formaldehyde.

Where the textile fibre material to be stabilized is a dyed textile fibre material, as is preferred, then particularly suitable dyes are disperse dyes of low solubility in water. Consequently, they are present in the dyeing liquor mostly in the form of a fine dispersion. They may belong to various dye classes, for example the acridone, azo, anthraquinone, coumarin, methine, perinone, naphthoquinoneimine, quinophthalone, styrene or nitro dyes. It is also possible in accordance with the invention to employ mixtures of disperse dyes.

Dyeing takes place from an aqueous liquor by a continuous or batch procedure. In the case of the batch procedure (exhaust procedure) the liquor ratio can be chosen within a wide range, for example from 1:1 to 10:10, preferably from 1:6 to 1:50. The temperature at which dyeing is carried out is at least 50° C. and generally not more than 140° C. It is preferably within the range from 80° to 135° C.

In the case of continuous dyeing procedures the dyeing liquors, which in addition to the dyes may include further auxiliaries, are applied to the piece material by means, for example, of pad-mangling, spraying or knit padding, and are developed using thermofix or HT steam processes.

Linear polyester fibres and cellulose fibres are preferably dyed by the high-temperature process in closed and pressure-resistant apparatus at temperatures >100° C., preferably between 110° and 135° C., and at atmospheric or superatmospheric pressures. Examples of suitable closed vessels are circulation apparatus, such as cheese or beam dyeing apparatus, winch becks, jet or drum dyeing machines, muff dyeing apparatus, paddles or jiggers.

Secondary cellulose acetate fibres are preferably dyed at temperatures of 80°–85° C.

Where the novel stabilizer mixtures are employed in the dyeing application, then application is preferably such that, for example, the fibre material is first of all treated with these stabilizer mixtures and then dyeing is conducted, or, preferably, the fibre material is treated simultaneously with a stabilizer mixture and with the dye in the dyebath. However, the stabilizer mixtures can also be applied subsequently to the finished dyeing by means of thermofixing, for example at from 190° to 230° C. within a period of from 30 seconds to 5 minutes. It is also possible to pretreat textile material with a novel stabilizer mixture, in which case the textile material is dimensionally stabilized at the same time.

The dyeing liquors may also include further additives, examples being dyeing assistants, dispersants, carriers, wool protectors, wetting agents and antifoams.

The dyebaths may additionally contain mineral acids, examples being sulfuric acid or phosphoric acid, or, more expediently, organic acids, for example aliphatic carboxylic acids such as formic acid, acetic acid, oxalic acid or citric acid, and/or salts, such as ammonium acetate, ammonium sulfate or sodium acetate. The purpose of the acids in particular is to establish the pH of the liquors used in accordance with the invention, which is preferably between 4 and 5.

The bath, containing the dye, a stabilizer mixture and, if desired, further additives, and having been adjusted to a pH from 4.5 to 5.5, is preferably entered initially with the fibre material, at from 40° to 80° C. for 5 minutes, and then the temperature is raised to 125-1 30° C. over the course of from 10 to 20 minutes and treatment is continued at this temperature for from 15 to 90 minutes, preferably for 30 minutes.

The dyeings are finished by cooling the dyeing liquor to from 50° to 80° C., rinsing the dyeings with water, and, if desired, reduction-clearing them in a customary manner in an alkaline medium. The dyeings are then rinsed again and dried. Where vat dyes are used for the cellulose portion, the goods are customarily treated first of all with hydrosulfite at a pH of from 6 to 12.5 and then with an oxidizing agent, and finally are rinsed out.

For the preparation of prints, the novel stabilizer mixtures are added in the form of their aqueous dispersions to the printing pastes. The printing paste comprises the appropriate stabilizer mixture in amounts of, for example, from 0.1 to 10%, preferably from 0.1 to 5%, based on the weight of the printing paste.

The amount of dyes added to the printing pastes depends on the desired shade; in general amounts of from 0.01 to 15 percent by weight, preferably from 0.02 to 10 percent by weight, based on the textile material employed, have been found to be appropriate.

In addition to the dyes and the aqueous stabilizer mixture dispersion, the printing pastes expediently comprise acid-stable thickeners, preferably of natural origin, such as cornflour derivatives, especially sodium alginate on its own or as a mixture with modified cellulose, in particular with preferably from 20 to 25 percent by weight of carboxymethylcellulose. In addition, the printing pastes may also include acid donors, such as butyrolactone or sodium hydrogen phosphate, preservatives, sequestering agents, emulsifiers, water-insoluble solvents, oxidizing agents or deaerating agents.

Particularly suitable preservatives are formaldehyde donors, such as paraformaldehyde or trioxane, especially aqueous formaldehyde solutions with concentrations of from about 30 to 40 percent by weight; examples of suitable sequestering agents are sodium nitrilotriacetate, sodium ethylenediaminetetraacetate, and especially sodium polymetaphosphate, especially sodium hexametaphosphate; particularly suitable emulsifiers are adducts of an alkylene oxide and a fatty alcohol, in particular an adduct of oleyl alcohol and ethylene oxide; suitable water-insoluble solvents are high-boiling saturated hydrocarbons, especially paraffins with a boiling range of from about 160° to 210° C. (solvent naphthas); examples of suitable oxidizing agents are an aromatic nitro compound, especially an aromatic mono- or dinitrocarboxylic or -sulfonic acid, which may possibly be in the form of an alkylene oxide adduct, in particular a nitrobenzenesulfonic acid; and examples of suitable deaerating agents are high-boiling solvents, especially turpentine oils, higher alcohols, preferably $C_8$- to $C_{10}$ alcohols, terpene alcohols or deaerating agents based on mineral oils and/or silicone oils, especially commercial formulations of from about 15 to 25 percent by weight of a mineral and silicone oil mixture and from about 75 to 85 percent by weight of a $C_8$ alcohol such as 2-ethyl-n-hexanol.

In the course of printing the fibre materials, the printing paste is applied directly to the entire area, or sections, of the fibre material, advantageously using printing machines of customary construction, for example inkjet printing, vigoureux printing, intaglio printing, rotary screen printing or planographic printing machines.

After printing, the fibre material is dried at temperatures up to 150° C., preferably from 80° to 120° C.

The material is then stabilized by heat treatment at temperatures of preferably from 100° to 220° C. Heat treatment is generally effected under pressure using superheated steam.

Depending on temperature, this stabilization may take from 20 seconds to 10 minutes, preferably from 4 to 8 minutes.

The prints are finished likewise in a customary manner by rinsing with water, and finishing can, if desired, be undertaken by additional reduction clearing in an alkaline medium, for example using sodium dithionite. In the latter case, the prints are again rinsed, dewatered and dried.

The textile fibres treated with the novel stabilizer mixtures exhibit good resistance to the damaging effect of light, oxygen and heat. In particular, it is possible using the novel process to obtain highly lightfast and sublimation-resistant polyester dyeings and prints. Specific pretreatment or aftertreatment of the fibre material is unnecessary with the novel process.

In the Examples which follow the percentages are by weight. The amounts of the dyes and UV absorbers are based on pure substance.

EXAMPLE 1

984 g of ice are introduced with stirring into a mixture of 541.4 g of cyanuric chloride in 1327 g of xylene (isomer mixture). Then, with thorough stirring, 1130 g of a 21 percent aqueous solution of sodium methylmercaptide are run in over the course of 10 minutes, during which the internal temperature rises to about 30° C. Stirring is continued for one hour. After phase separation the lower, aqueous phase is separated off. The organic phase is washed once with 885 g of water, to give 2044 g of a xylene solution which contains 18% by weight 1-methylthio-3,5-dichloro-s-triazine and 7.1% by weight 1,3-bis-methylthio-5-chloro-s-triazine.

EXAMPLE 2

63.71 g of anhydrous aluminium chloride are introduced at 25° C. and with thorough stirring into 200 g of the xylene solution obtained in Example 1, containing 36 g of 1-methylthio-3,5-dichloro-s-triazine and 14.2 of 1,3-bis-methylthio-5-chloro-s-triazine. The mixture is stirred for 15 minutes. Then a solution of 52.64 g of resorcinol in 110 g of sulfolane is added dropwise to the reaction mixture over the course of 1.5 h. During this time, the reaction temperature is raised from an initial 45° C. to about 50° C. Finally, condensation is completed by stirring at 70°0 C. for 1.5 h more and then at 80° C. for one hour. The emulsion-like mixture is cooled to 50° C. and the Friedel-Crafts complex is hydrolyzed by careful drop-wise addition of a mixture of 62 g of 32% hydrochloric acid and 455 g of water. The xylene is then removed by azeotropic distillation and the product suspension is filtered with suction. The filter material is rinsed with hot water and dried under reduced pressure at 80° C., to give 78.1 g of a powder containing the compounds of the formulae

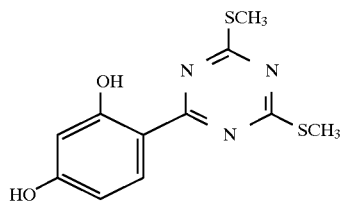

A and

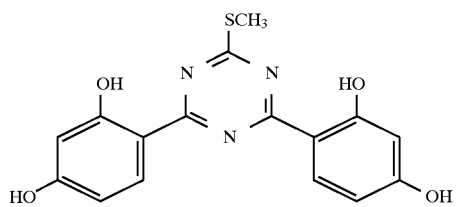

B in a weight ratio A:B of 15:85.

EXAMPLE 3

60 ml of 2N sodium hydroxide solution are added dropwise to a suspension of 20 g of the product mixture obtainable in Example 2 in 180 ml of methyl ethyl ketone. Then 13.99 g of dimethyl sulfate are added dropwise to the mixture over the course of one hour at from 33° to 35° C. The mixture is subsequently stirred for 16 h and the product mixture is neutralized with 2N hydrochloric acid. The organic solvent is separated off by azeotropic distillation, and finally the crystalline products are separated off by filtration. The filter residue is rinsed with water and dried under reduced pressure at 70° C., to give a powder containing the compounds of the formulae C, D and E

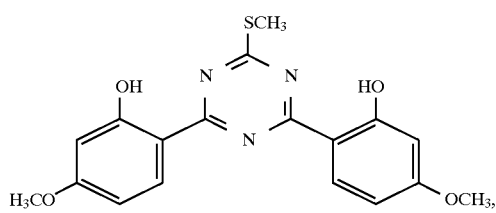

C

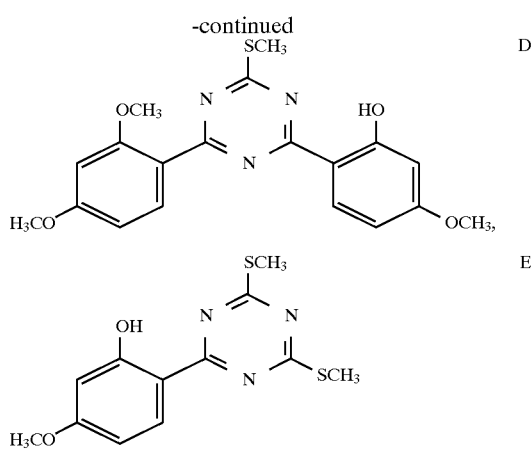

in a weight ratio of 71:13:16.

EXAMPLE 4

The procedure described in Example 3 is repeated but using, instead of 13.99 g of dimethyl sulfate, 17.88 g of diethyl sulfate and maintaining the reaction temperature at 40° C.; this gives a product mixture which essentially comprises the compounds of the formulae

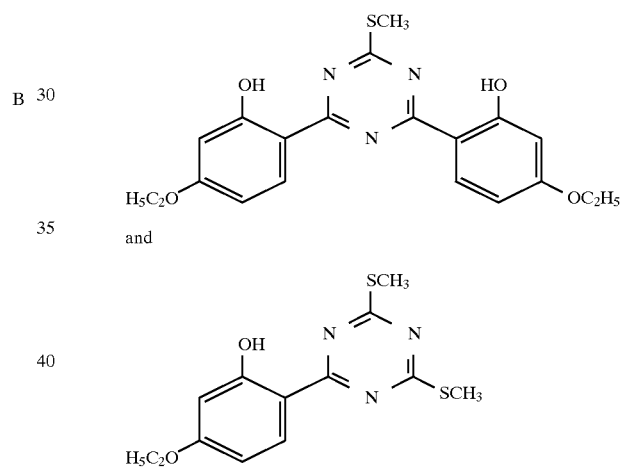

EXAMPLE 5

15.4 g of sodium methyl mercaptide as a 21 percent aqueous solution are added dropwise at 80° C. over the course of one hour to a toluene solution of 28.7 g of 1-methylthio-3,5-dichloro-s-triazine (prepared as in GB-A-1,176,770, Example 1). Then 50 ml of water are added and the mixture is subsequently stirred at 90°–95° C. for one hour more. The mixture is cooled to room temperature, and ice/ice-water and 100 ml of 1N sodium hydroxide solution are added. After stirring for a short time, the organic phase is separated off, washed with water again and dried over calcium chloride. 14.7 g of anhydrous aluminium(III) chloride are introduced into 121.5 g of the resulting toluene solution, containing 17.1% by weight 1,3-bismethylthio-5-chloro-s-triazine. A solution of 12.1 g of resorcinol and 25 ml of sulfolane is then added dropwise over the course of 25 minutes at a temperature of from 45° to 50° C. Stirring is subsequently carried out at 75° C. for 3 h. The emulsion is cooled to about 60° C. and the Friedel-Crafts complex is carefully decomposed with a mixture of 15 ml of conc. hydrochloric acid and 200 ml of water. Toluene is separated off by azeotropic distillation and the product suspension is filtered with suction. The residue is washed thoroughly with hot water and pressed. The crude product is recrystallized from water/dioxane to give the compound of the formula

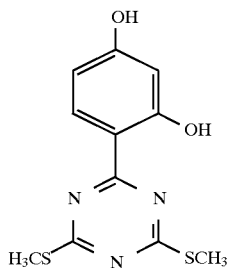

as a powder.

EXAMPLE 6

3.37 g of sodium carbonate are added to a suspension of 8.43 g of the compound of Example 5 in 27.9 g of dimethyl methylphosphonate, and the mixture is heated at 120° C. for 2¾ h. The reaction mixture is cooled to 75°–80° C., and a mixture of 70 ml of methanol and 20 ml of water is added dropwise. After cooling to room temperature, the solid precipitate is filtered off with suction, then washed with a little methanol and, finally, washed thoroughly with hot water. It is dried under reduced pressure at 70° C. and is purified by recrystallization from petroleum ether/dioxane, to give the compound of the formula

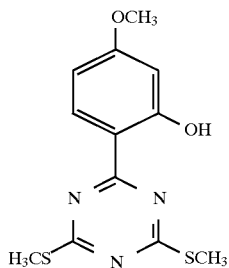

as a white powder.

EXAMPLE 7

250 g of ice are introduced with stirring into a mixture of 92.2 g of cyanuric chloride in 400 ml of toluene. Subsequently a solution of 61.9 g of sodium ethanethiolate in 250 ml of water is added dropwise with thorough stirring over the course of about 1.5 h, during which the internal temperature rises gradually to about 30° C. Stirring is continued at about 48° C. for 15 minutes more, and the mixture is left to cool. Following phase separation, the aqueous phase is separated off and the organic phase is washed three times with 500 ml portions of water, to give, after drying over calcium chloride, 590.9 g of a toluene solution containing 11.5% by weight of 1-ethylthio-3,5-dichloro-s-triazine and 3.48% by weight of 1,3-bisethylthio-5-chloro-s-triazine.

EXAMPLE 8

95.8 g of anhydrous aluminium(III) chloride are introduced with thorough stirring at room temperature into 564.5 g of the toluene solution from Example 7, and with gentle heating a red solution forms. Heating is continued to 40° C., and a solution of 79.2 g of resorcinol in 165 ml of sulfolane is added dropwise over the course of 1.5 h. During this time the internal temperature rises to 57° C. The emulsion is subsequently stirred at 80° C. for 4 h. The reaction mass, cooled to about 50° C., is discharged onto 1000 g of ice/250 ml of water. Toluene is subsequently removed by azeotropic distillation, and the aqueous product suspension is filtered. The residue is washed thoroughly with hot and cold water until it gives a neutral reaction to congo. Drying under reduced pressure at 80° C. gives 133.7 g of a bright yellow powder containing the compounds of the formulae

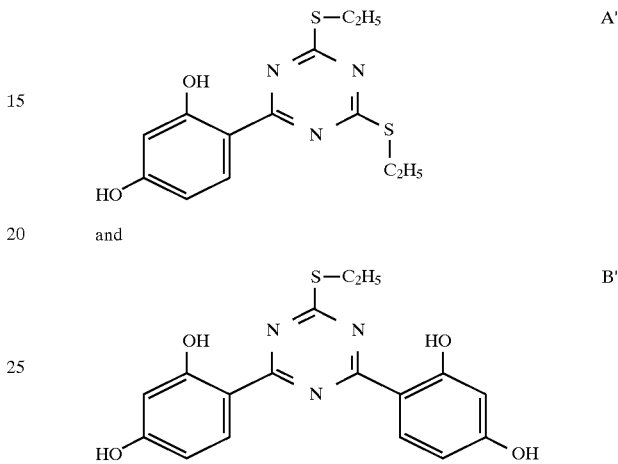

in a weight ratio A':B' of 24:76.

EXAMPLE 9

91.8 ml of 2N sodium hydroxide solution are introduced dropwise into a mixture of 20 g of the product from Example 8 in 100 ml of water, during which the temperature is held at 20° C. Then 18.5 g of dimethyl sulfate are introduced dropwise over the course of 1.5 h, during which the pH of the reaction mixture is kept constant at 11 by simultaneous dropwise addition of 2N sodium hydroxide solution. The mixture is subsequently stirred at room temperature for 21 h and filtered. The residue is suspended again in water and neutralized with dilute hydrochloric acid. After refiltration, the residue is washed thoroughly with water and dried under reduced pressure at 70° C., to give a beige powder containing the compounds of the formulae

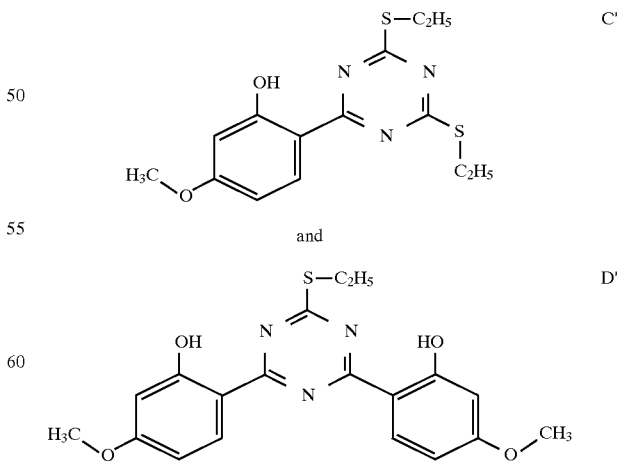

in a weight ratio C':D' of 22:78.

Dyeing Examples:

(i) Preparing a stabilizer formulation:

10 g of the stabilizer mixture obtained in Example 3, 20 ml of a 10% aqueous solution of the triethanolamine salt of tristyrylphenyl-polyethylene glycol-phosphoric acid and 25 g of quartz beads (1 mm in diameter) are placed in a high-speed stirrer and are ground for 16 hours. The ground material is then passed through a fine-meshed sieve to remove the glass beads, 0.5 g of xanthan gum (e.g. Biopolymer®AG) is added with stirring, and the formulation is adjusted with water to a stabilizer content of 10% by weight. The fineness of the dispersion is about 0.5–2 µm.

(ii) Use in exhaust dyeing::

A 10 g sample of a polyester tricot is dyed in an HT dyeing machine (e.g. Turbomat® from Mathis, Niederhasli) at a liquor ratio of 10:1. The aqueous dyeing liquor contains 2 g/l ammonium sulfate, 0.5 g/l dyeing assistant (Univadin® 3-flex), 0.5% by weight, based on the polyester tricot, of the UV absorber formulation prepared in (i), and 0.89% by weight, based on the polyester tricot, of a dye mixture comprising 18.5% by weight of dye $F_1$ of the formula

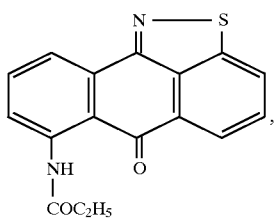

18.5% by weight of dye $F_2$ of the formula

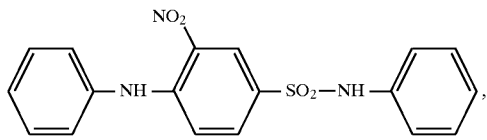

17.4% by weight of dye $F_3$ of the formula

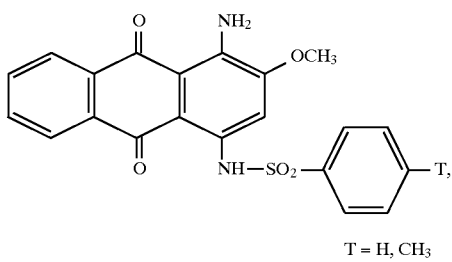

T = H, CH$_3$ 11.6% by weight of dye $F_4$ of the formula

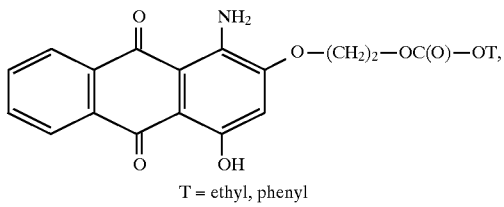

T = ethyl, phenyl 14.3% by weight of dye $F_5$ of the formula

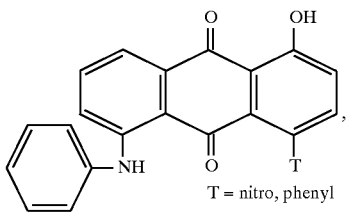

T = nitro, phenyl 10.2% by weight of dye $F_6$ of the formula

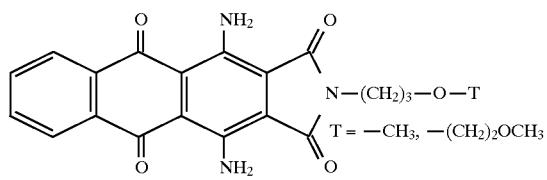

T = —CH$_3$, —(CH$_2$)$_2$OCH$_3$ and 9.5% by weight of dye $F_7$ of the formula

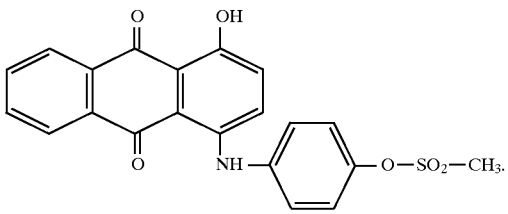

The dyeing liquor is adjusted with acetic acid to a pH of 5, homogenized and placed together with the tricot in a pressure dyeing pot. Dyeing is begun at 70° C., and then the contents are heated to 100° C. over the course of 10 minutes and to 130° C. over the course of a further 20 minutes. After a dyeing time of 30 minutes at this temperature, the contents are cooled to 50° C. and the dyed fabric is given a hot and cold rinse and reduction-cleaned at 70° C. with a liquor containing 3 ml/l of 30% sodium hydroxide solution and 2 g/l of sodium dithionite. Rinsing and drying give a polyester tricot which is dyed grey-violet and has very good hot light fastness.

(iii) If the procedure described under (ii) is repeated but the polyester tricot is dyed with a dyeing liquor which does not contain the stabilizer formulation prepared in (i), the hot light fastness of the resulting dyeing is markedly lower.

(iv) If the procedure described under (ii) is repeated but dyeing is carried out with a dyeing liquor which contains 1.15% by weight, based on the polyester tricot, of a dye mixture comprising 13% by weight each of dyes $F_1$ and $F_2$, 38.1% by weight of dye $F_3$, 25.4% by weight of dye $F_4$, 4.4% by weight of dye $F_5$, 3.2% by weight of dye $F_6$ and 2.9% by weight of dye $F_7$, a polyester tricot is obtained which is dyed wine-red and has very good hot light fastness.

(v) If the procedure described under (iv) is repeated but the polyester tricot is dyed with a dyeing liquor which does not contain the stabilizer formulation prepared in (i), a dyeing with a much lower hot light fastness is obtained.

Printing Example: For printing polyester textured tricot, a printing paste is prepared from a stock thickener, dyes and a stabilizer mixture.

The composition of the stock thickener is as follows:

| | |
|---|---|
| 120 g | Starch ether thickener |
| 480 g | Sodium alginate thickener |
| 5 g | Sodium hydrogen phopshate |
| 5 g | Printing assistant |
| 5 g | Sodium chlorate |
| 385 g | Deionized water |
| 1000 g | Stock thickener |

The printing paste has the following composition:
3.6 g of dye $F_2$ as in the Dyeing Example
3.4 g of a dye mixture comprising the dye $F_3$ as in the Dyeing Example and the dye of the formula

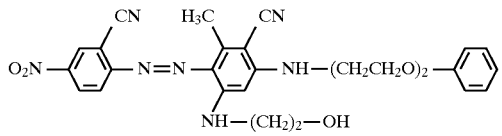

0.4 g of dye $F_7$ as in the Dyeing Example
1.6 g of dye $F_6$ as in the Dyeing Example
60 g of a stabilizer mixture according to Example 3, as a 20% ground formulation
931 g of stock thickener This printing paste is used to print cleaned pieces of polyester tricot on a printing table. The samples are then dried at 100° C. for 10 minutes and subsequently steamed with superheated steam at 1 80° C. for 8 minutes. The printed fabric is given hot and cold rinses and is reduction-cleared at 70° C. using a liquor containing 2 ml/l 30% sodium hydroxide solution and 3 g/l sodium dithionite. Rinsing and drying give a polyester tricot with a reddish beige print which has very good hot light fastness.

If the procedure described above is repeated but using a printing paste which does not contain the stabilizer formulation, a dyeing is obtained which has markedly lower hot light fastness.

What is claimed is:

1. A stabilizer mixture comprising at least one compound of the formula

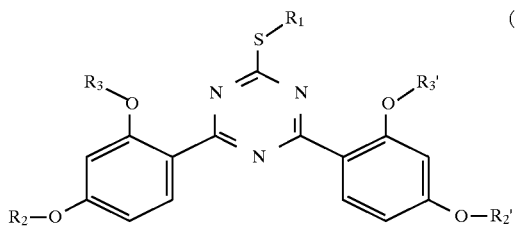

and at least one compund of the formula

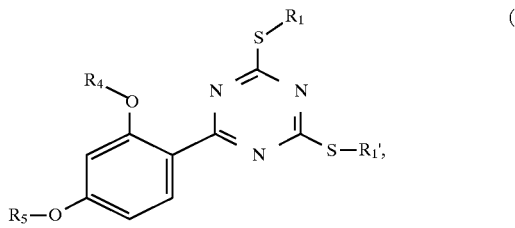

in which $R_1$ and $R_1'$ independently of one another are each linear or branched $C_1$–$C_{18}$alkyl, $C_3$–$C_8$cycloalkyl, $C_3$–$C_6$alkenyl, unsubstituted or $C_1$–$C_4$alkyl-, $C_1$–$C_4$alkoxy- or halo-substituted biphenyl, unsubstituted or $C_1$–$C_4$alkyl-, $C_1$–$C_4$alkoxy- or halo-substituted naphthyl, unsubstituted or $C_1$–$C_4$alkyl-, $C_1$–$C_4$alkoxy- or halo-substituted phenyl or $C_7$–$C_{12}$aralkyl, $R_2$, $R_2'$, $R_3$, $R_3'$, $R_4$ and $R_5$ independently of one another are each hydrogen, unsubstituted or halo-, cyano-, hydroxyl-, amino-, $C_1$–$C_4$alkoxycarbonyl-, carbamoyl, N-mono- or N,N-di-$C_1$–$C_4$alkyl carbamoyl-, glycidyl or phenyl-substituted linear or branched $C_1$–$C_{12}$alkyl, or linear or branched $C_4$–$C_{28}$alkyl, which is interrupted by one or more N, S or O atoms and which is unsubstituted or substituted by hydroxyl or by a radical —$OR_6$ or are a radical —CO—$R_6$ or —$SO_2$—$R_6$, and $R_6$ is $C_1$–$C_{12}$alkyl, unsubstituted or $C_1$–$C_4$alkyl-substituted phenyl or $C_7$–$C_{12}$aralkyl.

2. A stabilizer mixture according to claim 1, wherein $R_1$ and $R_1'$ independently of one another are each $C_1$–$C_6$alkyl, cyclohexyl which is unsubstituted or substituted by 1–3 methyl groups, allyl, isopropenyl, unsubstituted or $C_1$–$C_4$alkyl-, $C_1$–$C_4$alkoxy or halo-substituted phenyl, benzyl or α-methylbenzyl.

3. A stabilizer mixture according to claim 1, wherein $R_1$ and $R_1'$ are identical and are each $C_1$–$C_4$alkyl, cyclohexyl, allyl, phenyl or benzyl.

4. A stabilizer mixture according to claim 1, wherein $R_1$ and $R_1'$ are identical and are each methyl.

5. A stabilizer mixture according to claim 1, wherein $R_2$, $R_2'$, $R_3$, $R_3'$, $R_4$ and $R_5$ independently of one another are each hydrogen, $C_1$–$C_6$alkyl or straight-chain or branched $C_4$–$C_{28}$alkyl which is interrupted by one or more groups —O— and is substituted by hydroxyl or by a radical —$OR_6$, in which $R_6$ is $C_1$–$C_4$alkyl, phenyl, o-, m- or p-tolyl or benzyl, or are u nsubstituted or $C_1$–$C_4$alkyl-substituted benzoyl or phenylsulfonyl.

6. A stabilizer mixture according to claim 1, wherein $R_2$, $R_2'$, $R_3$, $R_3'$, $R_4$ and $R_5$ independently of one another are each hydrogen, $C_1$–$C_4$alkyl, a radical of the formula —$(CH_2CHR_7—O)_n$—H, in which $R_7$ is methyl or hydrogen and n is an integer from 1 to 9, or are benzoyl.

7. A stabilizer mixture according to claim 1, wherein $R_2$, $R_2'$ and $R_5$ independently of one another are each $C_1$–$C_4$alkyl, a radical of the formula —$(CH_2CHR_7—O)_n$—H, in which $R_7$ is methyl or hydrogen and n is an integer from 1 to 9, or are benzoyl, $R_3$ is hydrogen, $C_1$–$C_4$alkyl, a radical of the formula —$(CH_2CHR_7—O)_n$—H, in which $R_7$ is methyl or hydrogen and n is an integer from 1 to 9, or is benzoyl, and $R_3'$ and $R_4$ are each hydrogen.

8. A stabilizer mixture according to claim 1 wherein $R_2$, $R_2'$ and $R_5$ are identical and are each $C_1$–$C_4$alkyl, $R_3$ is hydrogen or $C_1$–$C_4$alkyl and $R_3'$ and $R_4$ are each hydrogen.

9. A stabilizer mixture according to claim 1 comprising essentially the compounds of the formula

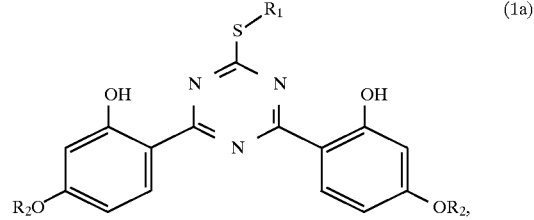

-continued

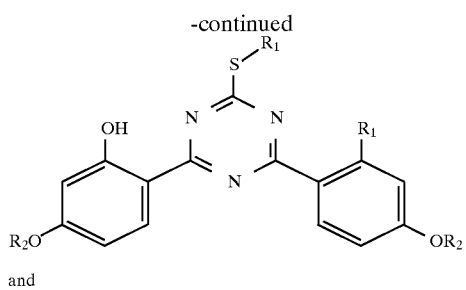

and

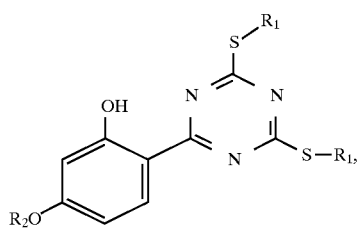

in which $R_1$ is linear or branched $C_1$–$C_{18}$alkyl, $C_3$–$C_8$cycloalkyl, $C_3$–$C_6$alkenyl, unsubstituted or substituted aryl or $C_7$–$C_{12}$aralkyl, and $R_2$ is hydrogen, unsubstituted or substituted linear or branched $C_1$–$C_{12}$alkyl, or linear or branched $C_4$–$C_{28}$alkyl which is interrupted by one or more N, S or O atoms and which may be substituted further or are a radical —CO—$R_6$ or —$SO_2$—$R_6$, and $R_6$ is $C_1$–$C_{12}$alkyl, unsubstituted or C–$C_4$alkyl-substituted phenyl or $C_7$–$C_{12}$aralkyl.

10. A stabilizer mixture according to claim 9, comprising from 50 to 95% by weight of compounds of the formulae (1a) and (1b) and from 50 to 5% by weight of the compound of the formula (2a).

11. A stabilizer mixture according to claim 9, comprising from 50 to 80% by weight of compounds of the formulae (1a) and (1b) and from 50 to 20% by weight of the compound of the formula (2a), in which $R_1C_1$–$C_4$alkyl, cyclohexyl, allyl, phenyl or benzyl and $R_2$ is $C_1$–$C_4$alkyl, a radical of the formula —$(CH_2CHR_4$—$O)_n$—H, in which $R_4$ is methyl or hydrogen and n is an integer from 1 to 9, or are benzoyl.

* * * * *